(12) United States Patent
Ishii et al.

(10) Patent No.: US 10,278,662 B2
(45) Date of Patent: May 7, 2019

(54) IMAGE PROCESSING APPARATUS AND MEDICAL IMAGE DIAGNOSTIC APPARATUS

(71) Applicant: Toshiba Medical Systems Corporation, Otawara-shi (JP)

(72) Inventors: Hideaki Ishii, Nasushiobara (JP); Takuya Sakaguchi, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 103 days.

(21) Appl. No.: 15/422,867

(22) Filed: Feb. 2, 2017

(65) Prior Publication Data

US 2017/0224300 A1 Aug. 10, 2017

(30) Foreign Application Priority Data

Feb. 5, 2016 (JP) .................................. 2016-021291
Dec. 26, 2016 (JP) .................................. 2016-251539

(51) Int. Cl.
| | |
|---|---|
| *G06K 9/00* | (2006.01) |
| *A61B 6/00* | (2006.01) |
| *A61B 6/03* | (2006.01) |
| *G06T 7/00* | (2017.01) |
| *G16H 50/50* | (2018.01) |

(52) U.S. Cl.
CPC ............ *A61B 6/5217* (2013.01); *A61B 6/032* (2013.01); *A61B 6/463* (2013.01); *A61B 6/469* (2013.01); *A61B 6/504* (2013.01); *A61B 6/507* (2013.01); *G06T 7/0012* (2013.01); *G16H 50/50* (2018.01); *A61B 6/563* (2013.01); *G06T 2207/10081* (2013.01); *G06T 2207/30104* (2013.01)

(58) Field of Classification Search
CPC ......... A61B 6/032; A61B 6/507; A61B 6/463; A61B 6/5217; A61B 5/02007
USPC .............................................. 382/131; 705/2
See application file for complete search history.

(56) References Cited

U.S. PATENT DOCUMENTS

| | | | |
|---|---|---|---|
| 8,548,778 B1 | 10/2013 | Hart et al. | |
| 8,768,669 B1 | 7/2014 | Hart et al. | |
| 8,768,670 B1 | 7/2014 | Hart et al. | |
| 8,914,264 B1 | 12/2014 | Hart et al. | |
| 2012/0041318 A1 | 2/2012 | Taylor | |
| 2012/0041319 A1 | 2/2012 | Taylor et al. | |

(Continued)

FOREIGN PATENT DOCUMENTS

| | | |
|---|---|---|
| JP | 2014-79649 | 5/2014 |
| JP | 2014-100249 | 6/2014 |

(Continued)

*Primary Examiner* — Charlotte M Baker
(74) *Attorney, Agent, or Firm* — Oblon, McClelland, Maier & Neustadt, L.L.P.

(57) ABSTRACT

An image processing apparatus according to an embodiment includes processing circuitry. The processing circuitry performs a fluid analysis using image data including a blood vessel to calculate an index value relating to blood flow in the blood vessel. The processing circuitry specifies a plurality of target sites in the blood vessel in the image data. The processing circuitry changes analysis conditions for the fluid analysis corresponding to the positions of the target sites. The processing circuitry causes a display to display, in a comparative manner, the index value relating to blood flow calculated under the changed analysis conditions for the target sites.

11 Claims, 13 Drawing Sheets

(56) References Cited

U.S. PATENT DOCUMENTS

| | | |
|---|---|---|
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0150516 A1 | 6/2012 | Taylor et al. |
| 2013/0054214 A1 | 2/2013 | Taylor |
| 2013/0064438 A1 | 3/2013 | Taylor et al. |
| 2013/0066618 A1 | 3/2013 | Taylor et al. |
| 2013/0151163 A1 | 6/2013 | Taylor et al. |
| 2013/0211728 A1 | 8/2013 | Taylor et al. |
| 2014/0046642 A1 | 2/2014 | Hart et al. |
| 2014/0107935 A1 | 4/2014 | Taylor |
| 2014/0148693 A1 | 5/2014 | Taylor |
| 2014/0155770 A1 | 6/2014 | Taylor |
| 2014/0164969 A1 | 6/2014 | Hart et al. |
| 2014/0173486 A1 | 6/2014 | Hart et al. |
| 2014/0207432 A1 | 7/2014 | Taylor |
| 2014/0222406 A1 | 8/2014 | Taylor |
| 2014/0236492 A1 | 8/2014 | Taylor |
| 2014/0236553 A1 | 8/2014 | Hart et al. |
| 2014/0243663 A1 | 8/2014 | Taylor |
| 2014/0247970 A1 | 9/2014 | Taylor |
| 2014/0249791 A1 | 9/2014 | Taylor |
| 2014/0249792 A1 | 9/2014 | Taylor |
| 2014/0292752 A1 | 10/2014 | Hart et al. |
| 2014/0316758 A1 | 10/2014 | Yagi et al. |
| 2014/0343906 A1 | 11/2014 | Yagi et al. |
| 2014/0348412 A1 | 11/2014 | Taylor |
| 2014/0350908 A1 | 11/2014 | Hart et al. |
| 2014/0355859 A1 | 12/2014 | Taylor et al. |
| 2015/0032435 A1 | 1/2015 | Yagi et al. |
| 2015/0073722 A1 | 3/2015 | Taylor et al. |
| 2015/0073761 A1 | 3/2015 | Hart et al. |
| 2015/0073766 A1 | 3/2015 | Hart et al. |
| 2015/0073767 A1 | 3/2015 | Hart et al. |
| 2015/0074610 A1 | 3/2015 | Hart et al. |
| 2015/0088015 A1 | 3/2015 | Taylor |
| 2015/0088478 A1 | 3/2015 | Taylor |
| 2015/0127031 A1 | 5/2015 | Yagi et al. |
| 2015/0150530 A1 | 6/2015 | Taylor et al. |
| 2015/0161326 A1 | 6/2015 | Taylor et al. |
| 2015/0161348 A1 | 6/2015 | Taylor et al. |
| 2015/0173700 A1 | 6/2015 | Hart et al. |
| 2015/0201849 A1 | 7/2015 | Taylor |
| 2015/0245776 A1 | 9/2015 | Hirohata et al. |
| 2015/0332015 A1 | 11/2015 | Taylor |
| 2015/0339459 A1 | 11/2015 | Taylor |
| 2015/0363941 A1 | 12/2015 | Taylor |
| 2015/0370995 A1 | 12/2015 | Wakai |
| 2015/0379230 A1 | 12/2015 | Taylor |
| 2016/0007945 A1 | 1/2016 | Taylor |
| 2016/0073991 A1 | 3/2016 | Taylor |
| 2016/0110517 A1 | 4/2016 | Taylor |
| 2016/0110866 A1 | 4/2016 | Taylor |
| 2016/0110867 A1 | 4/2016 | Taylor |
| 2016/0113528 A1 | 4/2016 | Taylor |
| 2016/0113726 A1 | 4/2016 | Taylor |
| 2016/0117815 A1 | 4/2016 | Taylor |
| 2016/0117816 A1 | 4/2016 | Taylor |
| 2016/0117819 A1 | 4/2016 | Taylor |
| 2016/0128661 A1 | 5/2016 | Taylor |
| 2016/0133015 A1 | 5/2016 | Taylor |
| 2016/0140313 A1 | 5/2016 | Taylor |
| 2016/0180055 A1 | 6/2016 | Fonte |
| 2016/0232667 A1 | 8/2016 | Taylor |
| 2016/0246939 A1 | 8/2016 | Taylor |
| 2016/0296287 A1 | 10/2016 | Taylor |
| 2016/0364859 A1 | 12/2016 | Taylor |
| 2016/0364860 A1 | 12/2016 | Taylor |
| 2016/0364861 A1 | 12/2016 | Taylor |
| 2016/0371455 A1 | 12/2016 | Taylor |
| 2018/0055572 A1* | 3/2018 | Spilker .................. G16H 50/20 |

FOREIGN PATENT DOCUMENTS

| | | |
|---|---|---|
| JP | 2014-188323 | 10/2014 |
| JP | 2015-134196 | 7/2015 |
| WO | WO 2013/031744 A1 | 3/2013 |

* cited by examiner

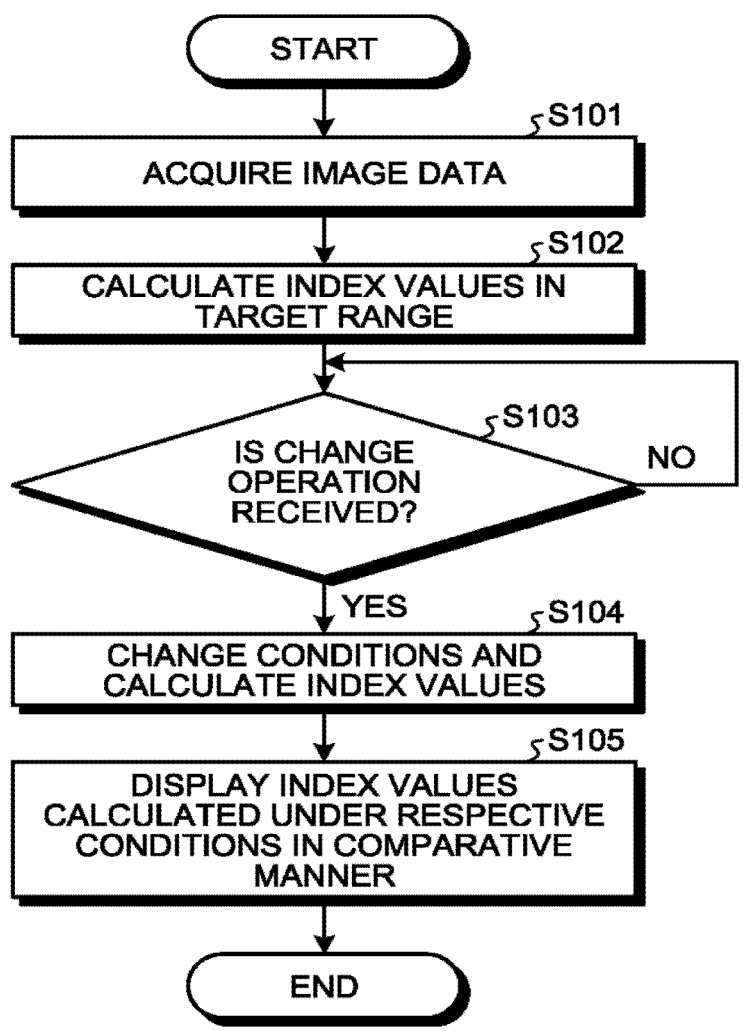

IMAGE PROCESSING APPARATUS AND MEDICAL IMAGE DIAGNOSTIC APPARATUS

CROSS-REFERENCE TO RELATED APPLICATIONS

This application is based upon and claims the benefit of priority from Japanese Patent Application No. 2016-021291, filed on Feb. 5, 2016 and Japanese Patent Application No. 2016-251539, filed on Dec. 26, 2016; the entire contents of which are incorporated herein by reference.

FIELD

Embodiments described herein relate generally to an image processing apparatus and a medical image diagnostic apparatus.

BACKGROUND

Conventionally known is the fact that the causes of ischemic diseases in organs are divided broadly into circulatory disorders and functional disorders in the organs themselves. A stenosis, which is an example of circulatory disorders in coronary arteries, is a serious lesion leading to an ischemic heart disease. In the case of such ischemic heart disease, it is necessary to determine whether to perform pharmacotherapy or stenting, for example. To carry out a diagnosis for evaluating hematogenous ischemia in coronary arteries, there has recently been a recommended method of measuring fractional flow reserve (FFR) using a pressure wire in coronary angiography (CAG) with a catheter.

By contrast, also known is a method of noninvasively evaluating hematogenous ischemia in coronary arteries using medical images of a heart acquired by a medical image diagnostic apparatus, such as an X-ray computed tomography (CT) apparatus, a magnetic resonance imaging (MRI) apparatus, and an ultrasonic diagnostic apparatus. As described above, hematogenous ischemia is evaluated by various methods, and treatment corresponding to the evaluation is performed. Recently, actual therapeutic effects are required to be determined before the treatment.

BRIEF DESCRIPTION OF THE DRAWINGS

FIG. 7 is a flowchart of a procedure performed by the image processing apparatus according to the first embodiment;

DETAILED DESCRIPTION

According to an embodiment, an image processing apparatus includes processing circuitry. The processing circuitry is configured to perform a fluid analysis using image data including a blood vessel to calculate an index value relating to blood flow in the blood vessel. The processing circuitry is configured to specify a plurality of target sites in the blood vessel in the image data. The processing circuitry is configured to change analysis conditions for the fluid analysis corresponding to positions of the target sites. The processing circuitry is configured to cause a display to display, in a comparative manner, the index value relating to blood flow calculated under the changed analysis conditions for the target sites.

Exemplary embodiments of an image processing apparatus and a medical image diagnostic apparatus according to the present application are described below in greater detail with reference to the accompanying drawings. The embodiments below are not intended to limit the image processing apparatus and the medical image diagnostic apparatus according to the present application.

First Embodiment

A first embodiment is described first. The first embodiment describes an example where the technique disclosed in the present application is applied to an image processing apparatus. The following describes an example where three-dimensional computed tomography (CT) image data is used as three-dimensional image data. In the following description, blood vessels of a heart are an object to be analyzed, for example.

Figure 1:
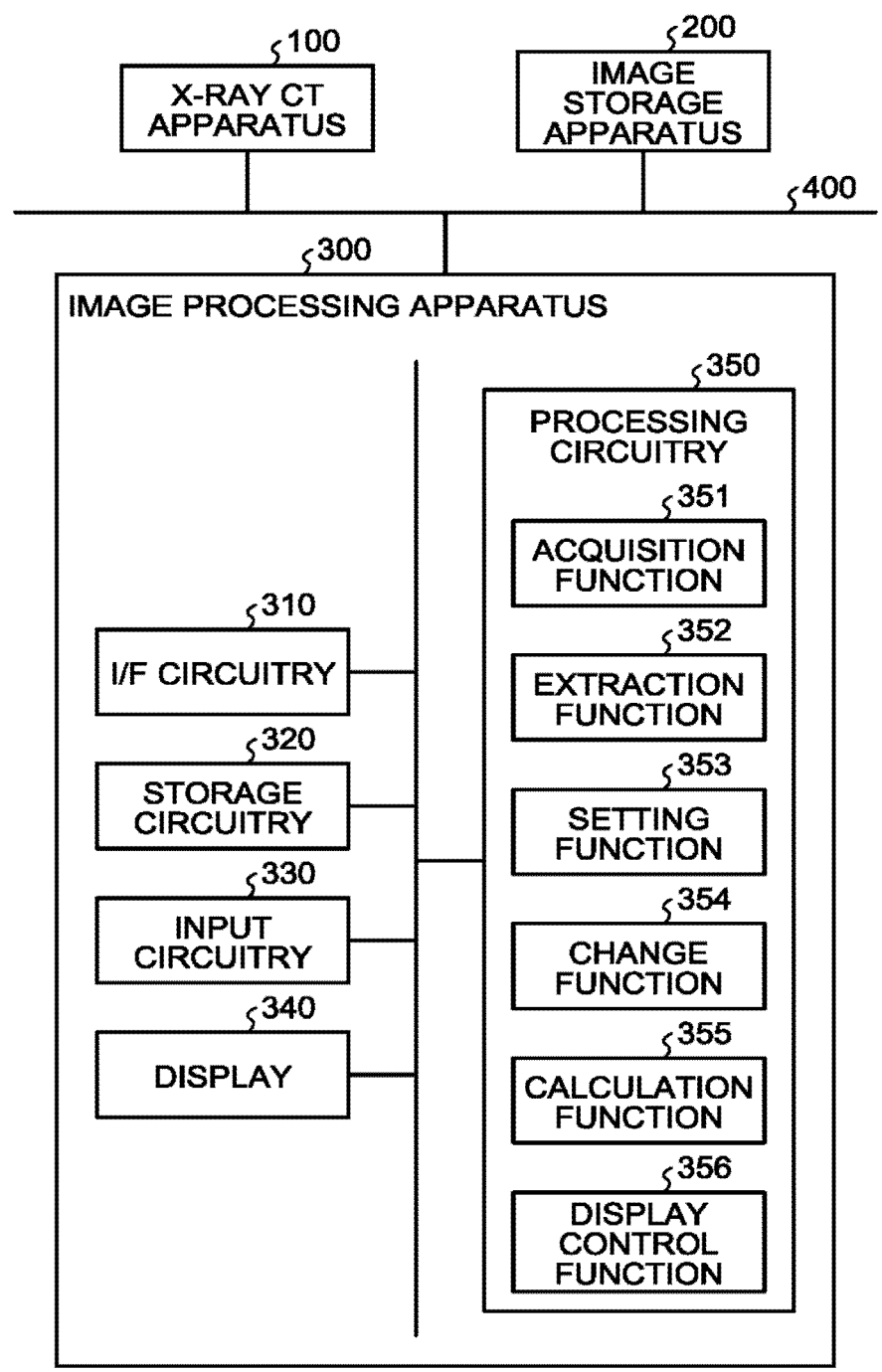
FIG. 1 is a diagram of an exemplary configuration of an image processing apparatus according to a first embodiment.

FIG. 1 is a diagram of an exemplary configuration of an image processing apparatus according to the first embodiment. As illustrated in FIG. 1, for example, an image processing apparatus 300 according to the first embodiment is connected to an X-ray CT apparatus 100 and an image storage apparatus 200 via a network 400. The image processing apparatus 300 may be further connected to other medical image diagnostic apparatuses, such as a magnetic resonance imaging (MRI) apparatus, an ultrasonic diagnostic apparatus, and a positron emission tomography (PET) apparatus, via the network 400.

The X-ray CT apparatus 100 acquires CT image data of a subject. Specifically, the X-ray CT apparatus 100 rotates an x-ray tube and an X-ray detector substantially about the subject. The X-ray CT apparatus 100 detects X-rays passing through the subject to acquire projection data. Based on the acquired projection data, the X-ray CT apparatus 100 generates time-series three-dimensional CT image data.

The image storage apparatus 200 stores therein image data acquired by various medical image diagnostic apparatuses. The image storage apparatus 200, for example, is provided as computer equipment, such as a server device. The image storage apparatus 200 according to the present embodiment acquires CT image data from the X-ray CT apparatus 100 via the network 400. The image storage apparatus 200 stores the acquired CT image data in storage circuitry provided inside or outside the apparatus.

The image processing apparatus 300 acquires image data from the various medical image diagnostic apparatuses via the network 400 and processes the acquired image data. The image processing apparatus 300, for example, is provided as computer equipment, such as a workstation. The image processing apparatus 300 according to the present embodiment acquires CT image data from the X-ray CT apparatus 100 or the image storage apparatus 200 via the network 400 and performs various types of image processing on the acquired CT image data. The image processing apparatus 300 displays the CT image data prior to or posterior to the image processing on a display or the like.

As illustrated in FIG. 1, for example, the image processing apparatus 300 includes interface (I/F) circuitry 310, storage circuitry 320, input circuitry 330, a display 340, and processing circuitry 350.

The I/F circuitry 310 is connected to the processing circuitry 350 to control transmission and communications of various types of data to and from the various medical image diagnostic apparatuses or the image storage apparatus 200 connected via the network 400. The I/F circuitry 310 is provided as a network card, a network adaptor, or a network interface controller (NIC), for example. The I/F circuitry 310 according to the present embodiment receives CT image data from the X-ray CT apparatus 100 or the image storage apparatus 200 and outputs the received CT image data to the processing circuitry 350.

The storage circuitry 320 is connected to the processing circuitry 350 to store therein various types of data. The storage circuitry 320 is provided as a semiconductor memory element, such as a random access memory (RAM) and a flash memory, a hard disk, or an optical disc, for example. The storage circuitry 320 according to the present embodiment stores therein CT image data received from the X-ray CT apparatus 100 or the image storage apparatus 200.

The input circuitry 330 is connected to the processing circuitry 350 to convert an input operation received from an operator into electrical signals and output them to the processing circuitry 350. The input circuitry 330 is provided as a trackball, a switch button, a mouse, a keyboard, and a touch panel, for example. The input circuitry 330, for example, receives an input operation for specifying a target site.

The display 340 is connected to the processing circuitry 350 to display various types of information and various types of image data output from the processing circuitry 350. The display 340 is provided as a liquid crystal monitor, a cathode ray tube (CRT) monitor, or a touch panel, for example.

The processing circuitry 350 controls the components in the image processing apparatus 300 based on an input operation received from the operator via the input circuitry 330. The processing circuitry 350 is provided as a processor, for example. The processing circuitry 350 according to the present embodiment stores CT image data output from the I/F circuitry 310 in the storage circuitry 320. The processing circuitry 350 reads CT image data from the storage circuitry 320 and displays it on the display 340.

With the configuration described above, the image processing apparatus 300 according to the present embodiment enables determination in advance of therapeutic effects on a circulatory disorder. Specifically, the image processing apparatus 300 performs a fluid analysis using a medical image (e.g., three-dimensional CT image data) including blood vessels, thereby calculating index values relating to blood flow. The image processing apparatus 300 changes analysis conditions used for the fluid analysis based on treatment and recalculates the index values relating to blood flow under the changed analysis conditions. The image processing apparatus 300 compares the index values obtained before and after the change in the analysis conditions, thereby enabling determination in advance of the therapeutic effects.

The image processing apparatus 300 calculates fractional flow reserve (FFR), a dynamic index in blood vessels, and an index relating to the flow rate of blood, for example, as the index values relating to blood flow. FFR is the ratio of the pressure at a proximal part closer to the heart in the blood vessels to the pressure at a distal part farther from the heart. FFR is expressed by "FFR=Pd(pressure at the distal part)/Pa (pressure at the proximal part)", for example. When a stenosis (target site) occurs in the blood vessels, for example, the stenosis reduces the pressure at the distal part, thereby reducing the value of FFR. The image processing apparatus 300 carries out a simulation to calculate how the value of FFR changes when treatment is performed on the target site. The image processing apparatus 300 thus enables determination in advance of the therapeutic effects. The image processing apparatus 300 can calculate the pressure, the vector, and the shear stress, for example, as the dynamic index in the blood vessels. The image processing apparatus 300 can calculate the flow rate and the flow speed, for example, as the index relating to the flow rate of blood.

The first embodiment describes determination of therapeutic effects on a stenosis occurring in coronary arteries, for example. The processing circuitry 350 according to the present embodiment includes an acquisition function 351, an extraction function 352, a setting function 353, a change function 354, a calculation function 355, and a display control function 356. The processing circuitry 350 is an example of a processing circuitry in the scope of claims.

The acquisition function 351 acquires time-series three-dimensional CT image data in which blood vessels of the subject are depicted. Specifically, the acquisition function 351 acquires three-dimensional CT image data from the X-ray CT apparatus 100 or the image storage apparatus 200 via the network 400. The acquisition function 351 stores the acquired three-dimensional CT image data in the storage circuitry 320.

The extraction function 352 extracts time-series blood vessel shape data indicating the shape of a blood vessel from the three-dimensional CT image data acquired by the acquisition function 351. Specifically, the extraction function 352 reads three-dimensional CT image data from the storage circuitry 320 and performs image processing on the read three-dimensional CT image data, thereby extracting the blood vessel shape data.

The extraction function 352 specifies a target area in which the index values are to be calculated in a blood vessel area included in the three-dimensional CT image data.

Specifically, the extraction function 352 specifies the target area in the blood vessel area by instructions or image processing performed by the operator via the input circuitry 330. The extraction function 352 extracts the blood vessel shape data in the specified target area from the three-dimensional CT image data. The blood vessel shape data includes: a core line of the blood vessel (coordinate information on the core line), the cross-sectional area of the blood vessel and a lumen on a cross section perpendicular to the core line, and the distance from the core line to the inner wall and the distance from the core line to the outer wall in the cylindrical direction on the cross section perpendicular to the core line, for example. The extraction function 352 extracts other various types of blood vessel shape data depending on the analysis method.

The setting function 353 sets analysis conditions for the fluid analysis. Specifically, the setting function 353 sets the material value of blood, conditions for iterative calculation, and the initial value for the analysis, for example, as the analysis conditions. The setting function 353 sets the viscosity and the density of blood, for example, as the material value of blood. The setting function 353 sets the maximum number of times of iteration in the iterative calculation, the relaxation coefficient, and the acceptable value of a residual, for example, as the conditions for iterative calculation. The setting function 353 sets the flow rate, the pressure, the fluid resistance, and the initial value of a pressure boundary, for example, as the initial value for the analysis. The various values used by the setting function 353 may be incorporated in the system in advance, interactively defined by the operator, or set using part of the functions of the calculation function 355.

The setting function 353 specifies a target site (e.g., a treatment target site) in the blood vessel in the image data. Specifically, the setting function 353 specifies a plurality of target sites in the blood vessel manually or automatically. The setting function 353, for example, specifies a range received via the input circuitry 330 as the target site. In this case, the input circuitry 330 receives a range (target site) in which the analysis conditions are to be changed, and the setting function 353 specifies the received range as the target site. Furthermore, the setting function 353 automatically specifies the target site based on the shape in the target area specified by the extraction function 352. The setting function 353, for example, extracts stenotic portions based on the shape in the target area and specifies, as the target site, a stenotic portion having a value equal to or higher than a certain degree of narrowing out of the extracted stenotic portions. The stenotic portions may be extracted by a desired method.

The change function 354 changes the analysis conditions for the fluid analysis performed on the target site in the blood vessel. Specifically, the change function 354 changes the blood vessel shape data extracted by the extraction function 352 and the analysis conditions set by the setting function 353. The change function 354 changes the pressure at the target site, a condition of a stent to be placed at the target site, the cross-sectional area at the target site, the shape at the target site, the target range of the analysis, or a procedure to be performed on the target site, for example. In other words, the change function 354 changes a parameter assumed to be changed by performing treatment on the target site, such as a stenosis. The calculation function 355, which will be described later, recalculates the index values. The processing performed by the change function 354 will be described later in detail.

The calculation function 355 calculates the index values relating to blood flow in the blood vessel by the fluid analysis using the image data including the blood vessel. Specifically, the calculation function 355 performs the fluid analysis using the blood vessel shape data extracted by the extraction function 352 and the analysis conditions set by the setting function 353, thereby calculating the index values relating to blood flow in the target area in the blood vessel. The calculation function 355, for example, calculates the index values, such as the pressure, the flow rate of blood, the flow speed of blood, the vector, and the shear stress at certain positions in the blood vessel, based on the blood vessel shape data, such as the outline of the lumen and the outer wall of the blood vessel and the cross-sectional area and the core line of the blood vessel, and on the set conditions, such as the material value of blood, the conditions for iterative calculation, and the initial value for the analysis. The calculation function 355 calculates the index values, such as FFR, from the calculated index values.

Figure 2:
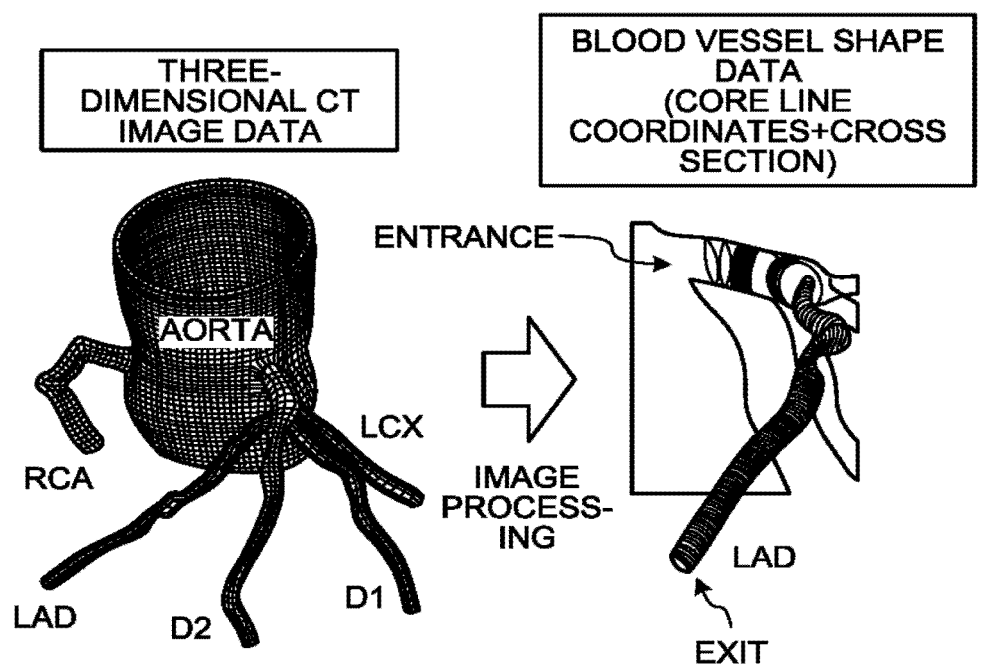
FIG. 2 is a diagram for explaining an example of processing according to the first embodiment.

FIG. 2 is a diagram for explaining an example of the processing according to the first embodiment. As illustrated in FIG. 2, for example, the extraction function 352 extracts the blood vessel shape data including the coordinates of the core line and the cross-sectional information on a LAD serving as the target area from the three-dimensional CT image data including an aorta and coronary arteries. The setting function 353 sets the analysis conditions for an analysis performed on the extracted LAD. The calculation function 355 performs the fluid analysis using the blood vessel shape data on the extracted LAD and the set conditions. The calculation function 355 thus calculates the index values, such as the pressure, the flow rate of blood, the flow speed of blood, the vector, and the shear stress, at certain positions along the core line from the boundary of the entrance of the target area LAD to the boundary of the exit thereof, for example. In other words, the calculation function 355 calculates distribution of the pressure, the flow rate of blood, the flow speed of blood, the vector, and the shear stress, for example, in the target area. The calculation function 355 calculates FFR at the positions in the target area based on the calculated distribution of pressure, for example.

As described above, the calculation function 355 performs the fluid analysis using the blood vessel shape data extracted by the extraction function 352 and the conditions set by the setting function 353, thereby calculating the index values relating to blood flow. The calculation function 355 according to the present embodiment performs the fluid analysis again using the conditions changed by the change function 354. In other words, the calculation function 355 performs the fluid analysis under the conditions changed on the assumption that treatment is performed on the target site, such as a stenosis. The calculation function 355 thus carries out a simulation on the index values resulting from the treatment.

The display control function 356 displays the index values relating to blood flow calculated by the calculation function 355 on the display 340. Specifically, the display control function 356 displays, on the display 340, the result of the fluid analysis performed before the change function 354 changes the conditions and the result of the fluid analysis performed after the change function 354 changes the conditions.

As described above, the image processing apparatus 300 according to the present embodiment changes the analysis conditions for the fluid analysis using the image data depending on the treatment contents. The image processing apparatus 300 performs the fluid analysis again under the changed conditions to calculate and display the index values. As a result, an observer can determine the therapeutic effects by checking the index values displayed by the image processing apparatus 300. The present embodiment changes the pressure at the target site, the cross-sectional area at the target site, the shape at the target site, or the target range of the analysis as the analysis conditions. In other words, the input circuitry 330 receives information on the contents of treatment to be performed on the target site and transmits it to the change function 354. The change function 354 changes the conditions described above depending on the treatment contents received via the input circuitry 330. The calculation function 355 calculates the index values under the changed conditions. The change in the conditions will be described below in order.

Change in the Pressure

Figure 3A:
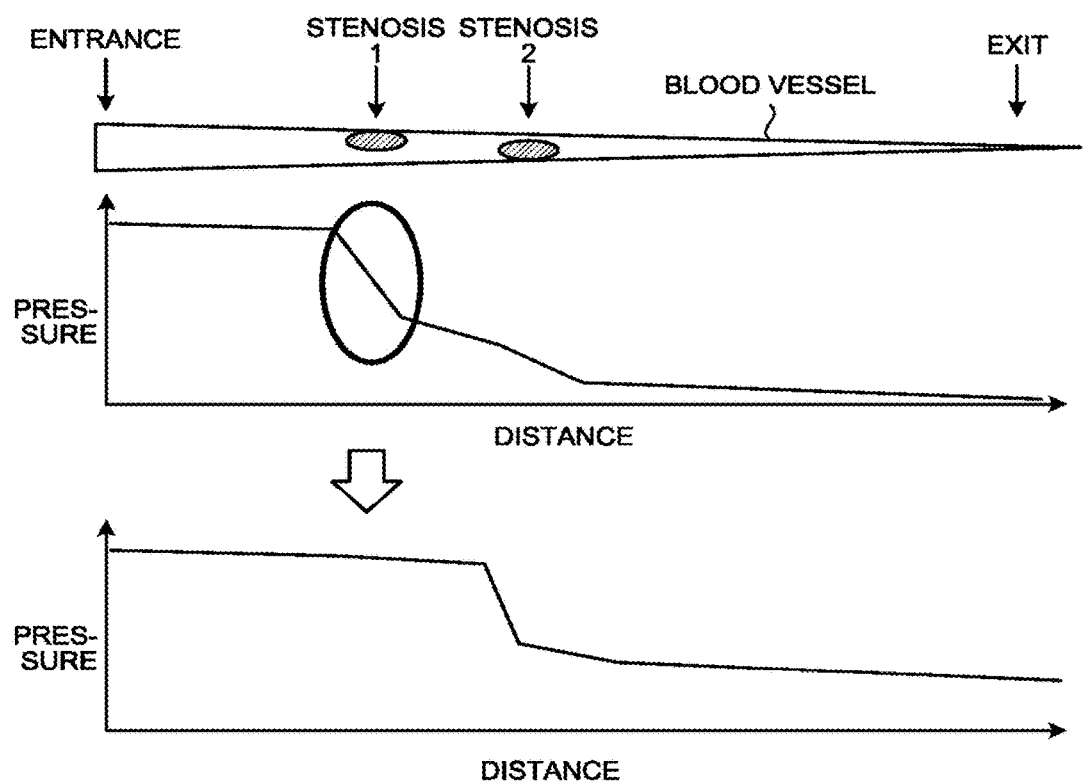
FIG. 3A is a diagram for explaining an example of change in the pressure according to the first embodiment.

The following describes a case where the pressure is changed. In this case, the change function 354 changes the initial value of the pressure in the fluid analysis depending on the treatment contents received by the input circuitry 330. When receiving the information that treatment is to be performed on a stenosis present at a certain position in the target area in the blood vessel, for example, the change function 354 changes the pressure at the certain position into a predetermined value. FIG. 3A is a diagram for explaining an example of the change in the pressure according to the first embodiment. In FIG. 3A, the upper diagram indicates the target area in the blood vessel, the middle diagram is a graph of the pressure distribution from the entrance to the exit obtained before the conditions are changed, and the lower diagram is a graph of the pressure distribution from the entrance to the exit obtained after the conditions are changed.

Let us assume a case where a "stenosis 1" and a "stenosis 2" serving as target sites are present in the target area in the blood vessel as illustrated in the upper diagram in FIG. 3A, for example. In this case, the change function 354 changes the conditions of the pressure depending on the treatment to be performed on these stenoses. To perform treatment of placing a stent at the "stenosis 1" illustrated in FIG. 3A, for example, the change function 354 changes the pressure at the position of the "stenosis 1" in the target area into a value corresponding to the treatment. The change function 354, for example, changes the value of the pressure based on information on pressure loss in a blood vessel with no stenosis. In other words, the change function 354 changes the value of the pressure at the position of the "stenosis 1" based on the information on pressure loss obtained when no stenosis is present in the distance from the entrance to the "stenosis 1" in the same blood vessel as that of the target area.

The change function 354, for example, changes the distribution of pressure surrounded by the ellipse in the middle diagram in FIG. 3A into the distribution of pressure at the corresponding position in the lower diagram in FIG. 3A. The calculation function 355 calculates the index values in the target area under the conditions of the pressure changed by the change function 354. In other words, the calculation function 355 performs the fluid analysis such that the pressure at the position of the "stenosis 1" is equal to the changed pressure, thereby calculating various index values. The display control function 356 displays the index values calculated by the calculation function 355 on the display 340. As illustrated in FIG. 3A, for example, the display control function 356 displays, on the display 340, FFR recalculated after the pressure at the position corresponding to the "stenosis 1" is changed into the predetermined value.

In a case where a plurality of target sites are included, the change function 354 can change the pressure at each of the target sites. The change function 354, for example, can change the pressure at the "stenosis 1" and the "stenosis 2" illustrated in FIG. 3A, and the calculation function 355 can calculate the index values under the respective changed conditions. In other words, the change function 354 can change the conditions at the respective target sites, and the calculation function 355 can calculate the index values under the respective conditions. The display control function 356 displays, in a comparative manner, the index values relating to blood flow calculated by the calculation function 355 under the respective analysis conditions changed by the change function 354 for the target sites in the blood vessel.

Figure 3B:
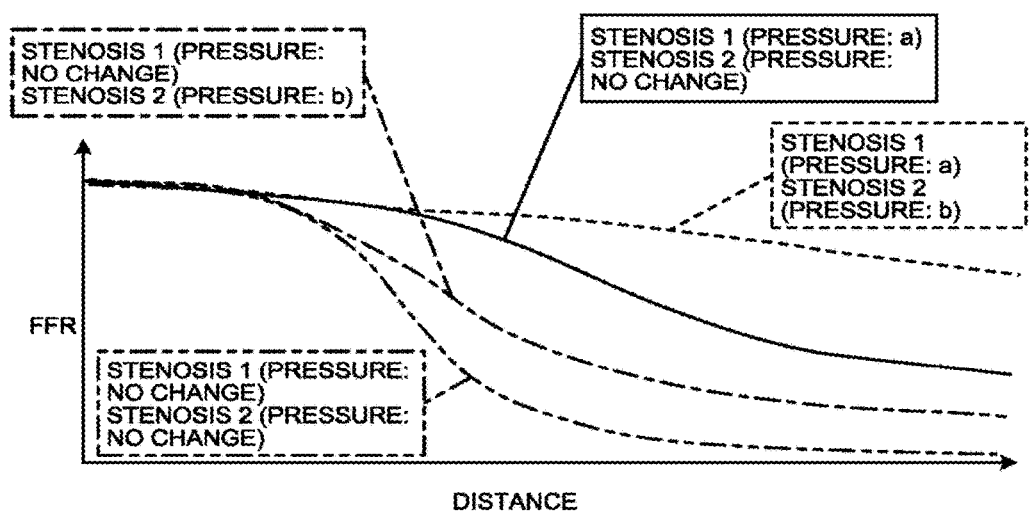
FIG. 3B is a diagram of an example of display information displayed by a display control function according to the first embodiment.

FIG. 3B is a diagram of an example of display information displayed by the display control function 356 according to the first embodiment. FIG. 3B illustrates the simulation results of FFR under the conditions in a case where the treatment is performed on the two stenoses in the blood vessel illustrated in FIG. 3A. As illustrated in FIG. 3B, for example, the display control function 356 displays the following analysis results in a comparative manner: the analysis result of FFR in "the stenosis 1 (pressure: no change) and the stenosis 2 (pressure: no change)" before the change, the analysis result of FFR in "the stenosis 1 (pressure: no change) and the stenosis 2 (pressure: b)" after the change, the analysis result of FFR in "the stenosis 1 (pressure: a) and the stenosis 2 (pressure: no change)" after the change, and the analysis result of FFR in "the stenosis 1 (pressure: a) and the stenosis 2 (pressure: b)" after the change.

The observer refers to the analysis results of FFR illustrated in FIG. 3B. Because the value of FFR is improved in "the stenosis 1 (pressure: a) and the stenosis 2 (pressure: no change)" than in "the stenosis 1 (pressure: no change) and the stenosis 2 (pressure: b)", the observer can determine that performing the treatment on the "stenosis 1" is more effective. Furthermore, the observer can readily determine whether to perform the treatment only the "stenosis 1" or both the "stenosis 1" and the "stenosis 2" based on the values of FFR.

Change in the Cross-Sectional Area

Figure 4A:
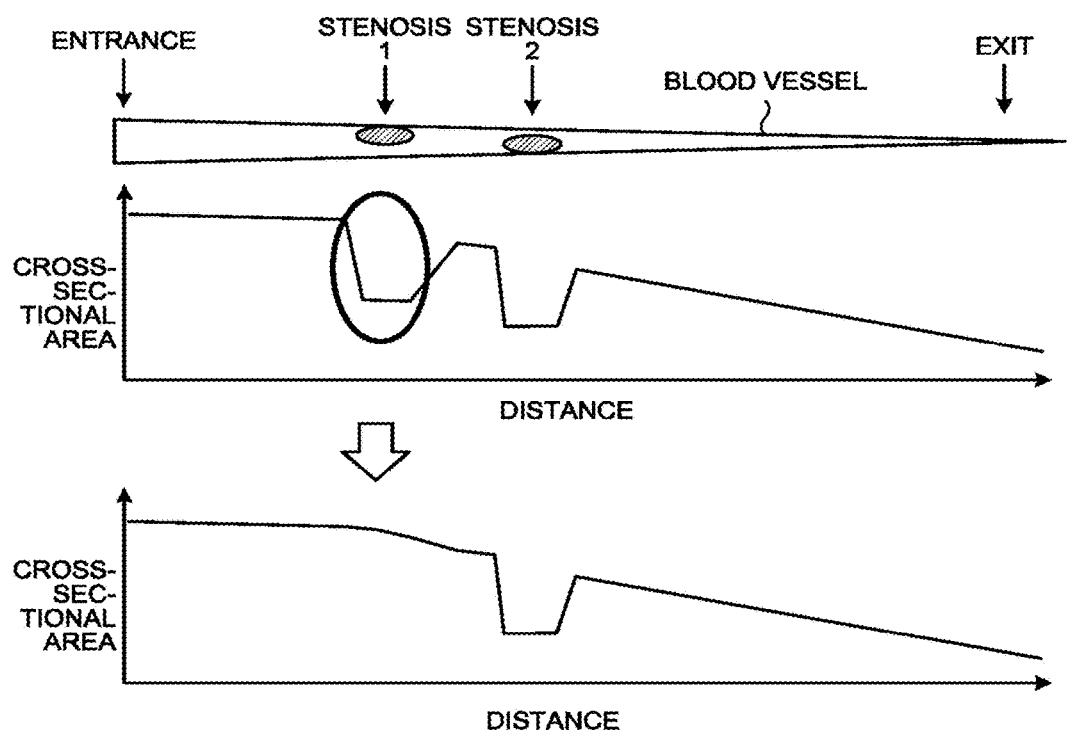
FIG. 4A is a diagram for explaining an example of change in the cross-sectional area according to the first embodiment.

The following describes a case where the cross-sectional area is changed. In this case, the change function 354 changes the value of the cross-sectional area in the fluid analysis depending on the treatment contents received by the input circuitry 330. When receiving the information that treatment is to be performed on a stenosis present at a certain position in the target area in the blood vessel, for example, the change function 354 changes the cross-sectional area at the certain position into a predetermined value. FIG. 4A is a diagram for explaining an example of the change in the cross-sectional area according to the first embodiment. In FIG. 4A, the upper diagram indicates the target area in the blood vessel, the middle diagram is a graph of the cross-sectional area of the blood vessel from the entrance to the exit obtained before the conditions are changed, and the lower diagram is a graph of the cross-sectional area of the blood vessel from the entrance to the exit obtained after the conditions are changed.

Let us assume a case where the "stenosis 1" and the "stenosis 2" serving as target sites are present in the target area in the blood vessel as illustrated in the upper diagram in FIG. 4A, for example. In this case, the change function 354 changes the conditions of the cross-sectional area depending on the treatment to be performed on these stenoses. To perform treatment of placing a stent at the "stenosis 1" illustrated in FIG. 4A, for example, the change function 354 changes the cross-sectional area at the position of the "stenosis 1" in the target area into a value corresponding to the cross-sectional area of the stent. The change function 354, for example, acquires the cross-sectional area at the cross section in the radial direction of the stent used for the treatment and changes the cross-sectional area at the position corresponding to the "stenosis 1" into the acquired cross-sectional area. In other words, the change function 354 changes the cross-sectional area of the cross section perpendicular to the core line at the position corresponding to the "stenosis 1" in the blood vessel shape data into the acquired cross-sectional area.

The change function 354, for example, changes the cross-sectional area in the area surrounded by the ellipse in the middle diagram in FIG. 4A into the cross-sectional area at the corresponding position in the lower diagram in FIG. 4A. The calculation function 355 calculates the index values in the target area under the conditions of the cross-sectional area changed by the change function 354. In other words, the calculation function 355 performs the fluid analysis by changing the cross-sectional area at the position of the "stenosis 1" in the blood vessel shape data, thereby calculating various index values. The display control function 356 displays the index values calculated by the calculation function 355 on the display 340. As illustrated in FIG. 4A, for example, the display control function 356 displays, on the display 340, FFR recalculated after the cross-sectional area at the position corresponding to the "stenosis 1" is changed into a value depending on the treatment.

Figure 4B:
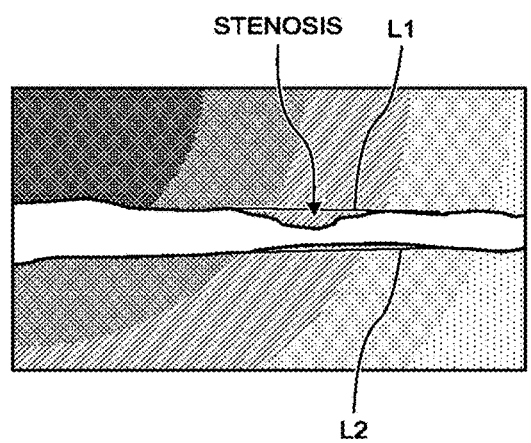
FIG. 4B is a diagram of an example of an operation for changing the cross-sectional area according to the first embodiment.

The cross-sectional area may be changed based on the size of the stent, or a change operation may be performed on an image by the observer. FIG. 4B is a diagram of an example of the operation for changing the cross-sectional area according to the first embodiment. FIG. 4B illustrates a curved multi-planar reconstruction (CPR) image of the target area in the blood vessel. As illustrated in FIG. 4B, for example, the extraction function 352 extracts the core line from the three-dimensional CT image data acquired by the acquisition function 351. The extraction function 352 generates the CPR image in which the blood vessel is exposed along the extracted core line. As illustrated in FIG. 4B, the extraction function 352 generates the CPR image such that a stenosis is depicted. The display control function 356 displays the generated CPR image on the display 340, and the input circuitry 330 receives an operation for changing the cross-sectional area. As illustrated in FIG. 4B, for example, the input circuitry 330 receives an operation for setting a line L1 and a line L2 on the CPR image.

Based on the line L1 and the line L2 received via the input circuitry 330, the extraction function 352 corrects the blood vessel shape data and re-extracts the cross-sectional area. In other words, the extraction function 352 re-extracts the cross-sectional area by considering the line L1 and the line L2 to be the wall of the lumen in the blood vessel (by erasing the stenotic area with the line L1 and the line L2). The CPR image illustrated in FIG. 4B may be displayed on the display 340 together with the analysis results of the index values. In other words, the display control function 356 displays the image indicating the shape resulting from the change in the cross-sectional area together with the analysis results. While FIG. 4B illustrates the CPR image viewed in one direction, the embodiment is not limited thereto. CPR images viewed in a plurality of directions, for example, may be displayed and used for the operation for changing the cross-sectional area.

Figure 4C:
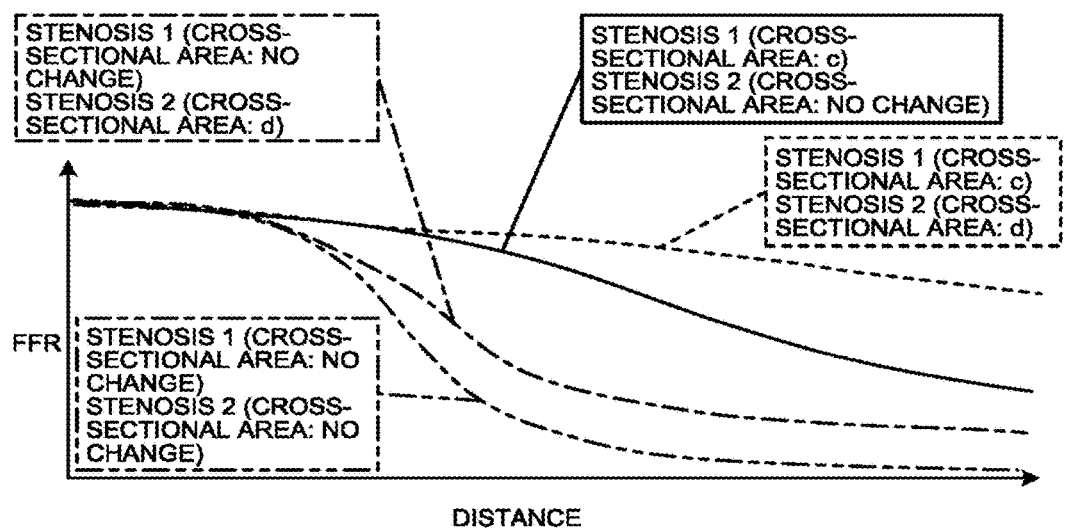
FIG. 4C is a diagram of an example of the display information displayed by the display control function according to the first embodiment.

Similarly to the change in the pressure, in a case where a plurality of target sites are included, the change function 354 can change the cross-sectional area at each of the target sites. The change function 354, for example, can change the cross-sectional area at the "stenosis 1" and the "stenosis 2" illustrated in FIG. 4A, and the calculation function 355 can calculate the index values under the respective changed conditions. FIG. 4C is a diagram of an example of the display information displayed by the display control function 356 according to the first embodiment. FIG. 4C illustrates the simulation results of FFR under the conditions in a case where the treatment is performed on the two stenoses in the blood vessel illustrated in FIG. 4A. As illustrated in FIG. 4C, for example, the display control function 356 displays the following analysis results in a comparative manner: the analysis result of FFR in "the stenosis 1 (cross-sectional area: no change) and the stenosis 2 (cross-sectional area: no change)" before the change, the analysis result of FFR in "the stenosis 1 (cross-sectional area: no change) and the stenosis 2 (cross-sectional area: d)" after the change, the analysis result of FFR in "the stenosis 1 (cross-sectional area: c) and the stenosis 2 (cross-sectional area: no change)" after the change, and the analysis result of FFR in "the stenosis 1 (cross-sectional area: c) and the stenosis 2 (cross-sectional area: d)" after the change. Similarly to the change in the pressure, the observer can refer to the analysis results of FFR illustrated in FIG. 4C to determine the therapeutic effects.

Change in the Diameter

Figure 5A:
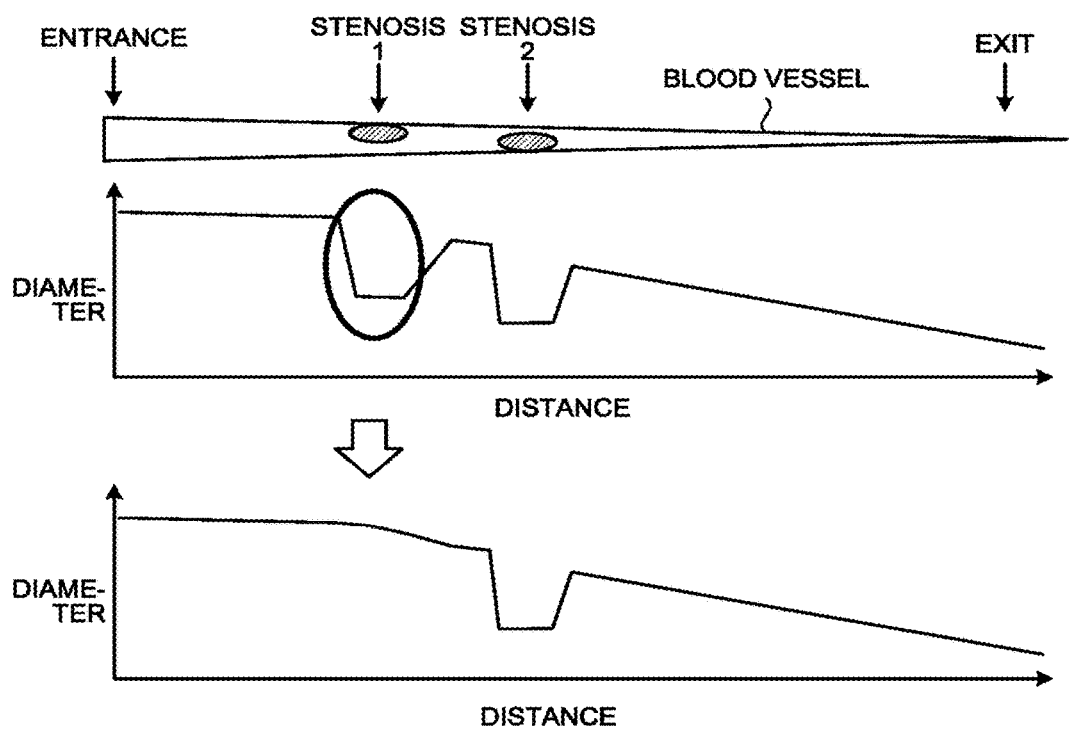
FIG. 5A is a diagram for explaining an example of change in the diameter according to the first embodiment.

The following describes a case where the diameter is changed. In this case, the change function 354 changes the value of the diameter in the fluid analysis depending on the treatment contents received by the input circuitry 330. When receiving the information that treatment is to be performed on a stenosis present at a certain position in the target area in the blood vessel, for example, the change function 354 changes the diameter at the certain position into a predetermined value. FIG. 5A is a diagram for explaining an example of the change in the diameter according to the first embodiment. In FIG. 5A, the upper diagram indicates the target area in the blood vessel, the middle diagram is a graph of the diameter of the blood vessel from the entrance to the exit obtained before the conditions are changed, and the lower diagram is a graph of the diameter of the blood vessel from the entrance to the exit obtained after the conditions are changed.

Let us assume a case where the "stenosis 1" and the "stenosis 2" serving as target sites are present in the target area in the blood vessel as illustrated in the upper diagram in FIG. 5A, for example. In this case, the change function 354 changes the conditions of the diameter depending on the treatment to be performed on these stenoses. To perform treatment of placing a stent at the "stenosis 1" illustrated in FIG. 5A, for example, the change function 354 changes the diameter at the position of the "stenosis 1" in the target area into a value corresponding to the diameter of the stent. The change function 354, for example, acquires the diameter of the stent used for the treatment and changes the diameter at the position corresponding to the "stenosis 1" into the acquired diameter. In other words, the change function 354 changes the diameter of the cross section perpendicular to the core line at the position corresponding to the "stenosis 1" in the blood vessel shape data into the acquired diameter.

The change function 354, for example, changes the diameter in the area surrounded by the ellipse in the middle diagram in FIG. 5A into the diameter at the corresponding position in the lower diagram in FIG. 5A. The calculation function 355 calculates the index values in the target area under the conditions of the diameter changed by the change function 354. In other words, the calculation function 355 performs the fluid analysis by changing the diameter at the position of the "stenosis 1" in the blood vessel shape data, thereby calculating various index values. The display control function 356 displays the index values calculated by the calculation function 355 on the display 340. As illustrated in FIG. 5A, for example, the display control function 356 displays, on the display 340, FFR recalculated after the diameter at the position corresponding to the "stenosis 1" is changed into a value depending on the treatment.

Figure 5B:
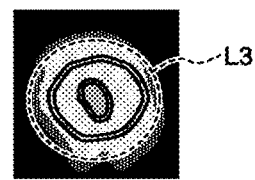
FIG. 5B is a diagram of an example of an operation for changing the diameter according to the first embodiment.

The diameter may be changed based on the size of the stent, or a change operation may be performed on an image by the observer. FIG. 5B is a diagram of an example of the operation for changing the diameter according to the first embodiment. FIG. 5B illustrates a multi-planar reconstruction (MPR) image of a cross section perpendicular to the core line corresponding to the position of the "stenosis 1". As illustrated in FIG. 5B, for example, the extraction function 352 extracts the core line from the three-dimensional CT image data acquired by the acquisition function 351. The extraction function 352 generates the MPR image of the cross section perpendicular to the core line at the position of the "stenosis 1". The display control function 356 displays the generated MPR image on the display 340, and the input circuitry 330 receives an operation for changing the diameter. As illustrated in FIG. 5B, for example, the input circuitry 330 receives an operation for setting a circle L3 on the MPR image.

Based on the circle L3 received via the input circuitry 330, the extraction function 352 corrects the blood vessel shape data and re-extracts the diameter. In other words, the extraction function 352 re-extracts the diameter by considering the circle L3 to be the wall of the lumen in the blood vessel. The MPR image illustrated in FIG. 5B may be displayed on the display 340 together with the analysis results of the index values. While FIG. 5B illustrates the MPR image of one cross section at the position corresponding to the "stenosis 1", the embodiment is not limited thereto. MPR images of a plurality of cross sections at the position corresponding to the "stenosis 1", for example, may be displayed and used for the operation for changing the diameter. Alternatively, the CPR image illustrated in FIG. 4B may be used for the operation for changing the diameter. On the contrary, the MPR image illustrated in FIG. 5B may be used for the operation for changing the cross-sectional area.

Figure 5C:
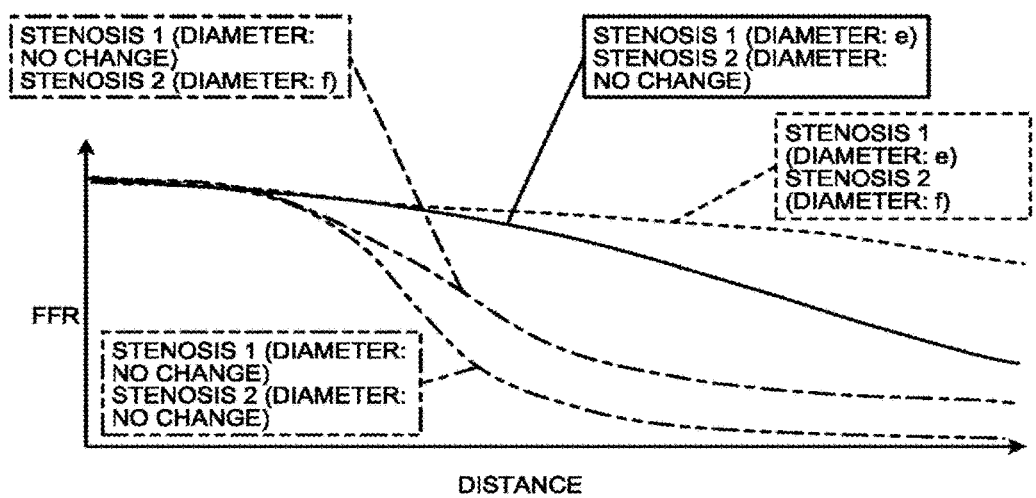
FIG. 5C is a diagram of an example of the display information displayed by the display control function according to the first embodiment.

In a case where a plurality of target sites are included, the change function 354 can change the diameter at each of the target sites. The change function 354, for example, can change the diameter at the "stenosis 1" and the "stenosis 2" illustrated in FIG. 5A, and the calculation function 355 can calculate the index values under the respective changed conditions. FIG. 5C is a diagram of an example of the display information displayed by the display control function 356 according to the first embodiment. FIG. 5C illustrates the simulation results of FFR under the conditions in a case where the treatment is performed on the two stenoses in the blood vessel illustrated in FIG. 5A. As illustrated in FIG. 5C, for example, the display control function 356 displays the following analysis results in a comparative manner: the analysis result of FFR in "the stenosis 1 (diameter: no change) and the stenosis 2 (diameter: no change)" before the change, the analysis result of FFR in "the stenosis 1 (diameter: no change) and the stenosis 2 (diameter: f)" after the change, the analysis result of FFR in "the stenosis 1 (diameter: e) and the stenosis 2 (diameter: no change)" after the change, and the analysis result of FFR in "the stenosis 1 (diameter: e) and the stenosis 2 (diameter: f)" after the change. The observer can refer to the analysis results of FFR illustrated in FIG. 5C to determine the therapeutic effects.

Change in the Range

Figure 6A:
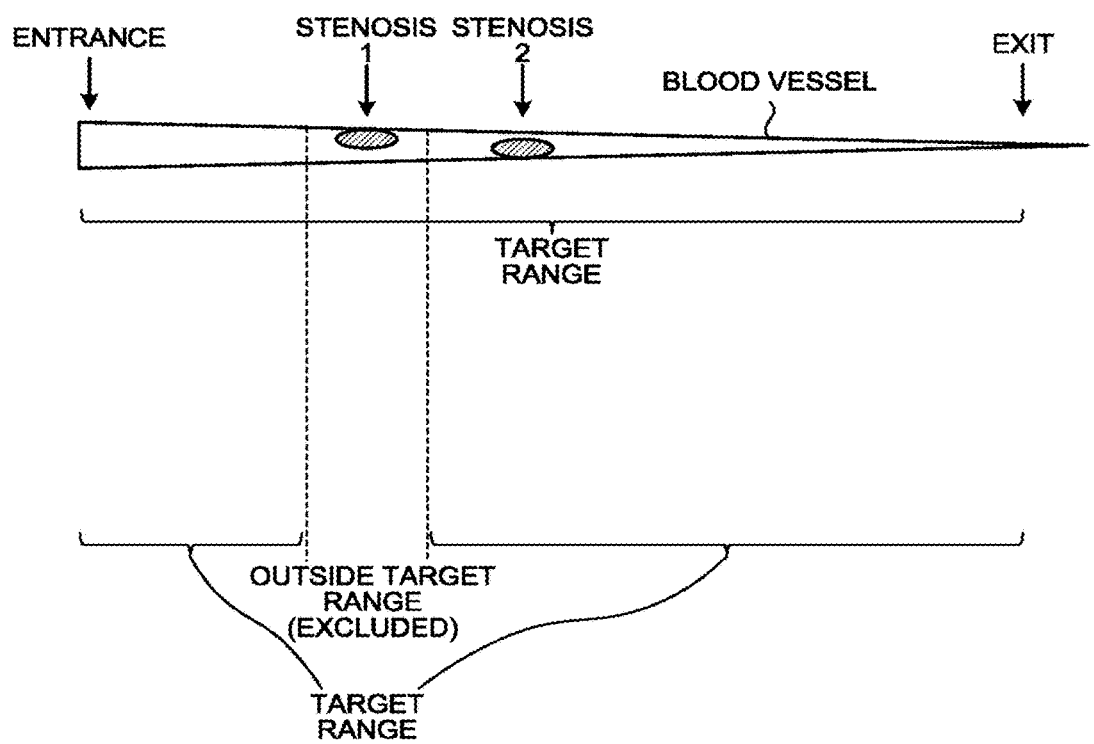
FIG. 6A is a diagram for explaining an example of change in the range according to the first embodiment.

The following describes a case where the range is changed. In this case, the change function 354 changes the analysis range of the fluid analysis depending on the treatment contents received by the input circuitry 330. When receiving the information that treatment is to be performed on a stenosis present at a certain position in the target area in the blood vessel, for example, the change function 354 changes the analysis range so as to exclude a certain position. FIG. 6A is a diagram for explaining an example of the change in the range according to the first embodiment. FIG. 6A illustrates the target area in the blood vessel and the analysis range before and after the change.

Let us assume a case where the "stenosis 1" and the "stenosis 2" serving as target sites are present in the target area in the blood vessel as illustrated in FIG. 6A, for example. In this case, the change function 354 changes the analysis range depending on the treatment to be performed on these stenoses. To perform treatment of placing a stent at the "stenosis 1" illustrated in FIG. 6A, for example, the change function 354 excludes the range corresponding to the "stenosis 1" in the target area to change the analysis range such that the other ranges serve as the target range as illustrated in FIG. 6A.

The calculation function 355 calculates the index values considering the range changed by the change function 354 to be the analysis target range. In other words, the calculation function 355 performs the fluid analysis by excluding the position of the "stenosis 1" in the blood vessel shape data, thereby calculating various index values. The calculation function 355, for example, uses the value of the pressure at the right end of the target range on the entrance side to calculate the value of the pressure at the left end of the target range on the exit side in FIG. 6A. In other words, the calculation function 355 calculates the index values relating to blood flow in the target range on the exit side using the values in the target range on the entrance side.

The display control function 356 displays the index values calculated by the calculation function 355 on the display 340. As illustrated in FIG. 6A, for example, the display control function 356 displays, on the display 340, FFR recalculated after the range corresponding to the "stenosis 1" is excluded.

Figure 6B:
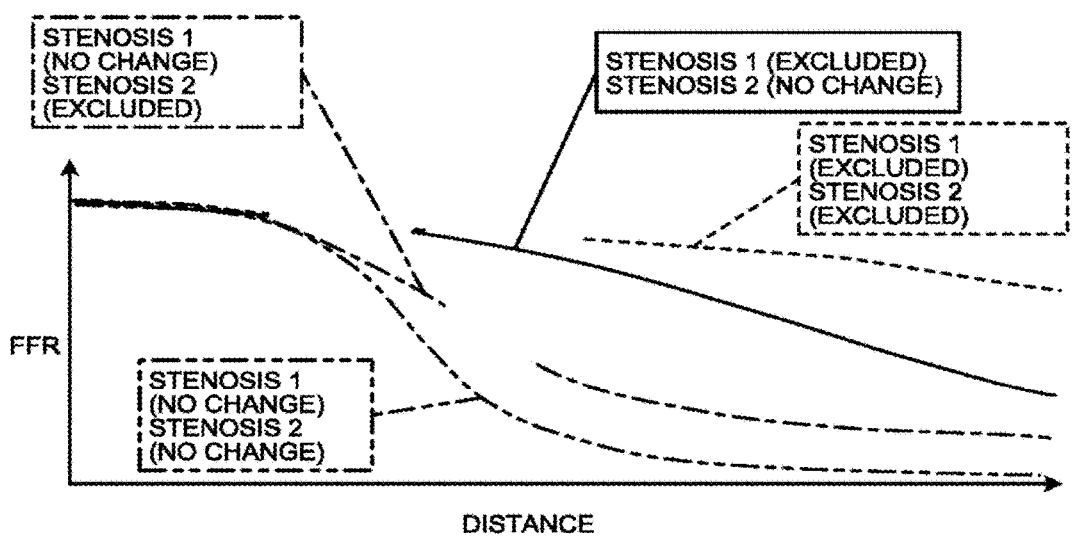
FIG. 6B is a diagram of an example of the display information displayed by the display control function according to the first embodiment.

In a case where a plurality of target sites are included, the change function 354 can change the range at each of the target sites. The change function 354, for example, can change the range at the "stenosis 1" and the "stenosis 2" illustrated in FIG. 6A and calculate the index values under the respective changed conditions. FIG. 6B is a diagram of an example of the display information displayed by the display control function 356 according to the first embodiment. FIG. 6B illustrates the simulation results of FFR under the conditions in a case where the treatment is performed on the two stenoses in the blood vessel illustrated in FIG. 6A. As illustrated in FIG. 6B, for example, the display control function 356 displays the following analysis results in a comparative manner: the analysis result of FFR in "the stenosis 1 (no change) and the stenosis 2 (no change)" before the change, the analysis result of FFR in "the stenosis 1 (no change) and the stenosis 2 (excluded)" after the change, the analysis result of FFR in "the stenosis 1 (excluded) and the stenosis 2 (no change)" after the change, and the analysis result of FFR in "the stenosis 1 (excluded) and the stenosis 2 (excluded)" after the change. The observer can refer to the analysis results of FFR illustrated in FIG. 6B to determine the therapeutic effects.

The processing functions included in the processing circuitry 350 have been described. The processing functions described above, for example, are stored in the storage circuitry 320 as computer programs that can be executed by a computer. The processing circuitry 350 reads the computer programs from the storage circuitry 320 and executes the read computer programs, thereby providing the processing functions corresponding to the respective computer programs. In other words, the processing circuitry 350 that reads the computer programs includes the processing functions illustrated in FIG. 1.

While FIG. 1 illustrates an example where the processing functions are provided by a single processing circuitry 350, the embodiment is not limited thereto. The processing circuitry 350 may be provided as a combination of a plurality of independent processors, for example. In this case, the processors may execute the computer programs, thereby providing the respective processing functions. The processing functions included in the processing circuitry 350 may be appropriately distributed or integrated in a single or a plurality of processing circuits.

The following describes the procedure performed by the image processing apparatus 300 according to the first embodiment. FIG. 7 is a flowchart of the procedure performed by the image processing apparatus 300 according to the first embodiment. Step S101 in FIG. 7, for example, is performed by the processing circuitry 350 reading and executing a computer program corresponding to the acquisition function 351 from the storage circuitry 320. Step S102 and Step S104, for example, are performed by the processing circuitry 350 reading and executing a computer program corresponding to the calculation function 355 from the storage circuitry 320. Step S103 and Step S104, for example, are performed by the processing circuitry 350 reading and executing a computer program corresponding to the change function 354 from the storage circuitry 320. Step S105, for example, is performed by the processing circuitry 350 reading and executing a computer program corresponding to the display control function 356 from the storage circuitry 320.

The processing circuitry 350 of the image processing apparatus 300 according to the present embodiment acquires time-series three-dimensional CT image data (Step S101). The processing circuitry 350 calculates the index values in the target range (Step S102). Subsequently, the processing circuitry 350 determines whether a change operation is received (Step S103). If a change operation is received (Yes at Step S103), the processing circuitry 350 changes conditions for the fluid analysis and recalculates the index values (Step S104). The processing circuitry 350 displays the index values calculated under the respective conditions in a comparative manner (Step S105).

As described above, the calculation function 355 according to the first embodiment performs a fluid analysis using image data including a blood vessel, thereby calculating index values relating to blood flow in the blood vessel. The change function 354 changes analysis conditions for the fluid analysis for a target site in the blood vessel. The display control function 356 displays, in a comparative manner, the index values relating to blood flow calculated by the calculation function 355 under the respective analysis conditions changed by the change function 354 for a plurality of target sites in the blood vessel. Consequently, the image processing apparatus 300 according to the first embodiment enables determination in advance of therapeutic effects on a circulatory disorder at the target sites.

The display control function 356 according to the first embodiment displays, in a comparative manner, the index values calculated under the respective analysis conditions in a manner associated with information indicating the analysis conditions used for the calculation. Consequently, the image processing apparatus 300 according to the first embodiment can facilitate the determination of the therapeutic effects on the target sites.

The change function 354 according to the first embodiment changes the pressure at the target site, a condition of a stent to be placed at the target site, the cross-sectional area at the target site, the shape at the target site, the target range of the analysis, or a procedure to be performed on the target site as the analysis conditions. Consequently, the image processing apparatus 300 according to the first embodiment can perform the fluid analysis on which the change caused by the treatment is reflected.

The calculation function 355 according to the first embodiment calculates at least one of FFR, the pressure, the flow rate of blood, the flow speed of blood, the vector, and the shear stress at positions in the blood vessel as the index values relating to blood flow. Consequently, the image processing apparatus 300 according to the first embodiment enables determination of the therapeutic effects using the various index values relating to blood flow.

As described above, the image processing apparatus 300 according to the first embodiment changes analysis conditions, calculates index values relating to blood flow, and displays the index values in a comparative manner. The image processing apparatus 300 thus enables determination in advance of therapeutic effects on a circulatory disorder at a plurality of target sites. Furthermore, the image processing apparatus 300 changes information relating to blood flow, such as the pressure, to calculate the index values. As a result, the image processing apparatus 300 can reduce the processing load and the processing time for the fluid analysis. In other words, the image processing apparatus 300 changes the information on the blood flow system and calculates the index values, thereby performing the fluid analysis without changing the shape of the blood vessel. With recent increase in definition of volume data, the data size increases. As a result, the processing load and the processing time for the fluid analysis may possibly increase. To address this, the image processing apparatus 300 according to the first embodiment performs the fluid analysis without changing the shape of the blood vessel by correcting the information on the blood flow system, such as the pressure. Consequently, the image processing apparatus 300 according to the first embodiment can reduce the processing load and the processing time.

Second Embodiment

The following describes a second embodiment. The configuration of an image processing apparatus according to the present embodiment is basically the same as that of the image processing apparatus 300 illustrated in FIG. 1. The following mainly describes differences of the image processing apparatus from the image processing apparatus 300 according to the first embodiment. Components having the same functions as those of the components illustrated in FIG. 1 are denoted by like reference numerals, and detailed explanation thereof is omitted.

The first embodiment determines the therapeutic effects by changing conditions depending on the treatment. By contrast, the second embodiment presents more effective treatment. To place a stent at a stenosis, for example, the image processing apparatus 300 according to the second embodiment carries out a simulation by changing the position at which the stent is to be placed and the size of the stent and presents the results.

Figure 8A:
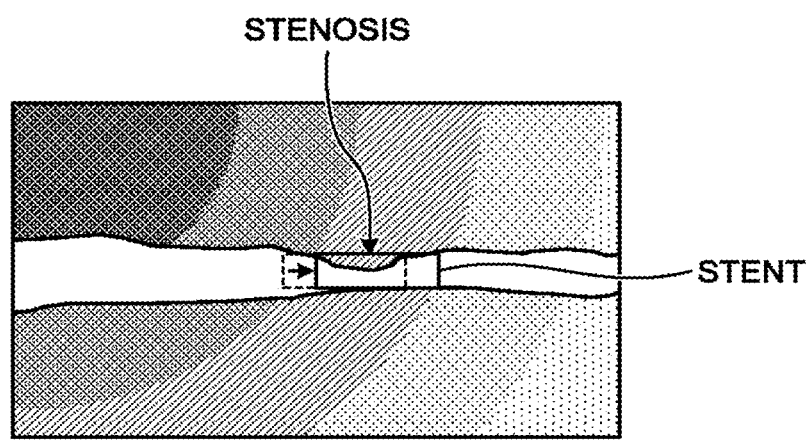
FIG. 8A is a diagram for explaining change in conditions of a stent made by a change function according to a second embodiment.
Figure 8B:
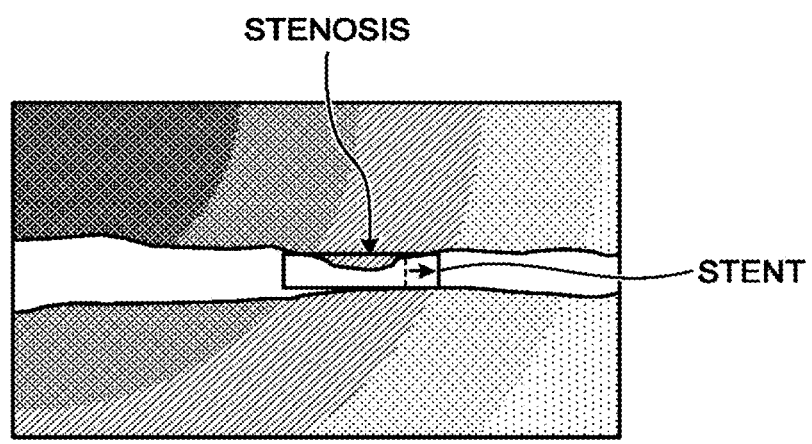
FIG. 8B is a diagram for explaining change in conditions of the stent made by the change function according to the second embodiment.

The change function 354 according to the second embodiment changes at least one of the position at which the stent is to be arranged, the length of the stent, and the diameter of the stent as the conditions of the stent. FIGS. 8A and 8B are diagrams for explaining change in the conditions of the stent made by the change function 354 according to the second embodiment. FIG. 8A illustrates a case where the position of the stent is changed. FIG. 8B illustrates a case where the length of the stent is changed.

As illustrated in FIG. 8A, for example, the change function 354 gradually changes the arrangement position of the stent with respect to the stenosis, and the calculation function 355 calculates the values of FFR at the respective arrangement positions. The change function 354, for example, shifts the position at which the stent is to be placed with the size of the stent fixed, and the calculation function 355 calculates the values of FFR at the respective positions. The display control function 356 presents information on the position having the largest value of FFR to the observer. As illustrated in FIG. 8A, for example, the display control function 356 displays, on the display 340, a CPR image provided with a stent image at the position having the largest value of FFR. As a result, the observer can readily grasp a more effective placement position of the stent.

As illustrated in FIG. 8B, for example, the change function 354 gradually changes the size of the stent to be placed at the stenosis, and the calculation function 355 calculates the values of FFR based on the respective sizes. In placement of a stent in the body, a stent having a smaller size less affects the subject. The change function 354 changes the size of the stent in ascending order, and the calculation function 355 calculates the values of FFR. The change function 354, for example, changes the size of the stent from that of the shortest stent to a predetermined length in order, and the calculation function 355 calculates the values of FFR based on the respective sizes. The change function 354, for example, changes the size of the stent from that of the stent having the smallest diameter to a predetermined size in order, and the calculation function 355 calculates the values of FFR based on the respective sizes.

The length and the diameter may have their upper limit based on the size of the blood vessel in which the stent is to be placed. In other words, the change function 354 sets the range between the lower limit and the upper limit of the length and the diameter of the stent to be placed based on the size of the blood vessel in which the stent is to be placed (e.g., the diameter and the thickness of the blood vessel wall). The change function 354 changes the stent from the stent having the shortest length or the smallest diameter within the set range in order, and the calculation function 355 calculates the values of FFR.

In a case where at least one of the length and the diameter of the stent is changed as the analysis conditions, the display control function 356 according to the second embodiment displays at least one of the shortest length and the smallest diameter of the stent having the value of FFR in the blood vessel exceeding a predetermined value. In other words, the display control function 356 displays information on the stent that least affects the subject out of the stents having high therapeutic effects. The display control function 356, for example, displays the conditions of the stent under which the value of FFR exceeds the predetermined value (e.g., 0.9) on the display 340.

Figure 9:
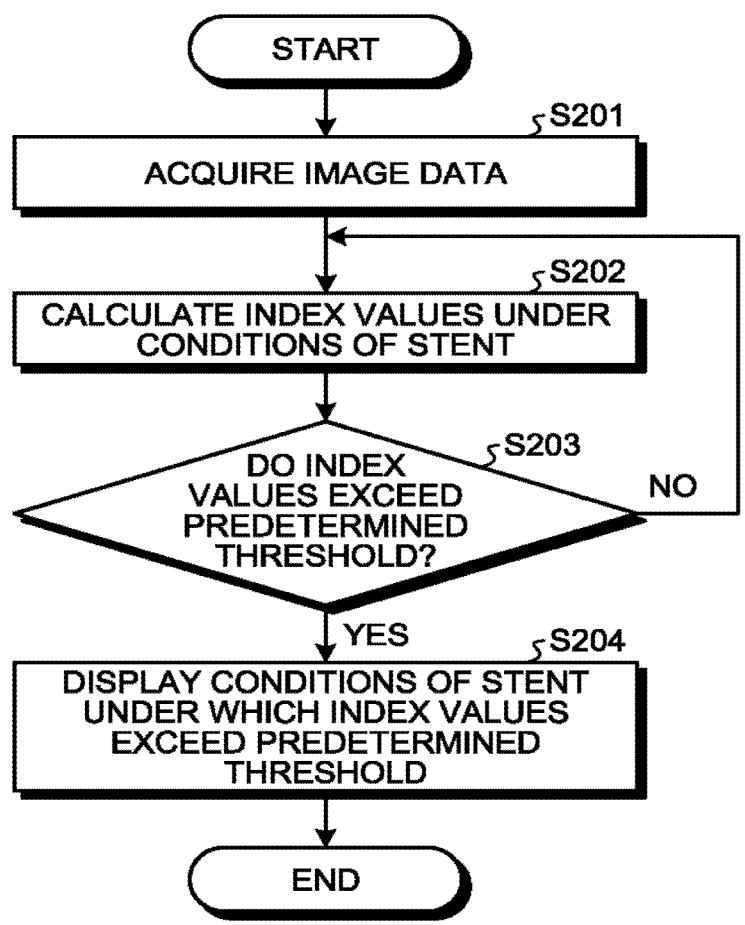
FIG. 9 is a flowchart of a procedure performed by the image processing apparatus according to the second embodiment.

The following describes the procedure performed by the image processing apparatus 300 according to the second embodiment. FIG. 9 is a flowchart of the procedure performed by the image processing apparatus 300 according to the second embodiment. Step S201 in FIG. 9, for example, is performed by the processing circuitry 350 reading and executing a computer program corresponding to the acquisition function 351 from the storage circuitry 320. Step S202, for example, is performed by the processing circuitry 350 reading and executing computer programs corresponding to the change function 354 and the calculation function 355 from the storage circuitry 320. Step S203 and Step S204, for example, are performed by the processing circuitry 350 reading and executing a computer program corresponding to the display control function 356 from the storage circuitry 320.

The processing circuitry 350 of the image processing apparatus 300 according to the present embodiment acquires time-series three-dimensional CT image data (Step S201). The processing circuitry 350 calculates the index values under conditions of a stent (Step S202). Subsequently, the processing circuitry 350 determines whether the index values exceed a predetermined threshold (Step S203). If the index values exceed the predetermined threshold (Yes at Step S203), the processing circuitry 350 displays the conditions of the stent under which the index values exceed the predetermined threshold (Step S204).

As described above, the change function 354 according to the second embodiment changes at least one of the position at which the stent is to be arranged, the length of the stent, and the diameter of the stent as the conditions of the stent. Consequently, the image processing apparatus 300 according to the second embodiment can present the conditions of the stent having high therapeutic effects.

In a case where at least one of the length and the diameter of the stent is changed as the analysis conditions, the display control function 356 according to the second embodiment displays at least one of the shortest length and the smallest diameter of the stent having the value of FFR in the blood vessel exceeding the predetermined value. Consequently, the image processing apparatus 300 according to the second embodiment can present the conditions of the stent that less affects the subject and that has high therapeutic effects.

Third Embodiment

While the first and the second embodiments have been described, the present application may be embodied in a variety of different forms besides the first and the second embodiments.

While the embodiments above calculate FFR as the index values relating to blood flow, the embodiments are not limited thereto. Alternatively, the embodiments may calculate the pressure, the flow rate, the flow speed, the vector, and the shear stress, for example. If the cross-sectional area and the diameter are changed, the embodiments may calculate the pressure, the flow rate, and the flow speed, for example. If the range or the shape are changed, the embodiments may calculate the pressure, the flow speed, the flow rate, the vector, and the shear stress, for example.

While the embodiments above change the cross-sectional area or the diameter of the blood vessel, the embodiments are not limited thereto. Alternatively, the embodiments may change the shape of the blood vessel, for example. For example, the embodiments may calculate FFR, the pressure, the flow speed, the flow rate, the vector, and the shear stress obtained in a case where a bypass is formed in the blood vessel.

While the embodiments above perform the processing on coronary arteries, the embodiments are not limited thereto. Alternatively, the embodiments may be used for determination of therapeutic effects obtained in a case where a stent is placed in carotid arteries or femoral arteries, for example.

While the embodiments above place a stent as the procedure to be performed on the target site, the embodiments are not limited thereto. Alternatively, the embodiments may employ various procedures. Specifically, the change function 354 changes the procedure to be performed on the target site. The following describes examples where the image processing apparatus 300 according to the first embodiment and the image processing apparatus 300 according to the second embodiment change the procedure to be performed on the target site.

In a case where the conditions are changed depending on the treatment as described in the first embodiment, for example, the change function 354 of the image processing apparatus 300 changes the procedure to be performed on a selected target site. The change function 354 changes the pressure at the target site, the cross-sectional area at the target site, the shape at the target site, or the target range of the analysis depending on the changed procedure. In other words, the change function 354 changes the conditions described above depending on the procedure contents (treatment contents) received via the input circuitry 330. The calculation function 355 calculates the index values under the changed conditions.

The input circuitry 330 receives an operation of specifying pharmacotherapy, directional coronary atherectomy (DCA), or rotational coronary atherectomy (Rotablator), for example, besides the placement of a stent described above as the procedure. If the input circuitry 330 receives an operation of specifying pharmacotherapy, for example, the change function 354 changes the pressure at the target site, the cross-sectional area at the target site, the shape at the target site, or the target range of the analysis depending on the effects of medications. The change function 354, for example, changes the pressure at the target site into a value corresponding to the contents of a pharmacotherapeutic plan input by a user (e.g., a value of the pressure based on information on pressure loss in a blood vessel with no stenosis).

Similarly, the change function 354 can change the cross-sectional area and the shape at the target site and the target range of the analysis into a value depending on the contents of the pharmacotherapeutic plan. The degree of the change depending on the pharmacotherapy may be optionally set. The degree of the change is set in advance depending on the type and the amount of medications, the sex and the age of the subject dozed with the medications, and the state of the target site, for example. Based on the information on these factors received via the input circuitry 330, the change function 354 changes the pressure at the target site, the cross-sectional area at the target site, the shape at the target site, or the target range of the analysis. If the procedure to be performed on the target site is pharmacotherapy, and the change function 354 changes the target range of the analysis, the change function 354 changes the target range of the analysis for all the target sites (treatment target sites) in the blood vessel.

If the input circuitry 330 receives an operation of specifying DCA or Rotablator, for example, the change function 354 changes the pressure at the target site, the cross-sectional area at the target site, the shape at the target site, or the target range of the analysis depending on the effects of change in the shape of the blood vessel presumed by a simulation of the procedure of DCA or Rotablator. The change function 354, for example, changes the pressure at the target site into a value corresponding to DCA or Rotablator (e.g., a value of the pressure presumed in a case where a calcified area to be excised in the target site is removed). The change function 354, for example, changes the value of the pressure into a value corresponding to the proportion of the calcified area to be excised by DCA or Rotablator.

Similarly, the change function 354 can change the cross-sectional area and the shape at the target site and the target range of the analysis into a value depending on the procedure contents of DCA or Rotablator. The degree of the change depending on DCA or Rotablator may be appropriately adjusted by receiving information on the proportion and the position of the calcified area to be excised, for example.

As described above, if the change function 354 changes the conditions, the calculation function 355 recalculates the index values under the changed conditions. The display control function 356 displays the index values calculated under the respective conditions in a comparative manner.

The following describes an example where the image processing apparatus 300 according to the second embodiment changes the procedure to be performed on the target site. In this case, the image processing apparatus 300 carries out a simulation by switching the contents of the procedure to be performed on the target site and presents the result.

The input circuitry 330, for example, receives an operation of specifying DCA and Rotablator as the type of the procedure for which a simulation on the target site is to be carried out. The change function 354 changes the value of the pressure at the target site into a value of the pressure corresponding to DCA and a value of the pressure corresponding to Rotablator. The calculation function 355 calculates the values of FFR based on the respective values of the pressure corresponding to DCA and the pressure corresponding to Rotablator. The display control function 356 presents, to the observer, information on a procedure by which the value of FFR is improved more. As a result, the observer can readily grasp a more effective procedure.

The embodiments above are not necessarily applied to a three-dimensional fluid analysis, and they may be applied to a two-dimensional or a one-dimensional fluid analysis.

While the embodiments above use the three-dimensional CT image data acquired by the X-ray CT apparatus as the time-series three-dimensional medical image data in which the blood vessels of the subject are depicted, the embodiments are not limited thereto. Alternatively, the embodiments may use medical images acquired by another medical image diagnostic apparatus as the time-series three-dimensional medical image data, for example. Specifically, the embodiments may use medical images acquired by an MRI apparatus or an ultrasonic diagnostic apparatus, for example.

While the image processing apparatus 300 according to the embodiments above performs the various types of processing, the embodiments are not limited thereto. Alternatively, a medical image diagnostic apparatus may perform the various types of processing, for example. In this case, the medical image diagnostic apparatus, such as an X-ray CT apparatus, an MRI apparatus, and an ultrasonic diagnostic apparatus, includes processing circuitry similar to the processing circuitry 350 and performs the processing described above using acquired medical image data.

The term "processor" used in the description of the embodiments above means a circuit, such as a central processing unit (CPU), a graphics processing unit (GPU), an application specific integrated circuit (ASIC), or a programmable logic device (e.g., a simple programmable logic device (SPLD), a complex programmable logic device (CPLD), and a field programmable gate array (FPGA)). The computer programs may be directly embedded in the circuit of the processor instead of being stored in the storage circuit. In this case, the processor reads and executes the computer programs embedded in the circuit, thereby providing the functions. The processors according to the present embodiment are not necessarily provided as individual circuits. The processors may be provided as one processor by combining a plurality of independent circuits to provide the functions.

The computer program executed by the processor is embedded and provided in a read only memory (ROM) or a storage unit, for example. The computer program may be recorded and provided in a computer-readable recording medium, such as a compact disk read only memory (CD-ROM), a flexible disk (FD), a compact disk recordable (CD-R), and a digital versatile disc (DVD), as an installable or executable file. The computer program may be stored in a computer connected to a network, such as the Internet, and provided or distributed by being downloaded via the network. The computer program has a module configuration including functional units, which will be described later. In actual hardware, the CPU reads and executes the computer program from a storage medium, such as a ROM, to load the modules on the main memory, thereby generating the modules on the main memory.

At least one of the embodiments above enables determination in advance of therapeutic effects on a circulatory disorder.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
   processing circuitry configured to
   generate blood vessel shape data based on image data including a blood vessel;
   set boundary conditions and analysis conditions in a fluid analysis;
   perform a fluid analysis based on the boundary conditions and the analysis conditions on the blood vessel shape data to calculate an index value relating to blood flow in the blood vessel;
   specify a plurality of target sites in the blood vessel in the image data;
   change analysis conditions for the fluid analysis corresponding to positions of the target sites without changing the blood vessel shape data to calculate an index value relating to blood flow under the changed analysis conditions for the target sites; and
   cause a display to display, in a comparative manner, the index value relating to blood flow calculated under the changed analysis conditions for the target sites.

2. The image processing apparatus according to claim 1, wherein the processing circuitry is configured to cause the display to display, in a comparative manner, a plurality of index values calculated under the respective analysis conditions in a manner associated with information indicating the analysis conditions used for the calculation.

3. The image processing apparatus according to claim 1, wherein the processing circuitry is configured to change pressure at each of the target sites, a condition of a stent to be placed at the target site, a cross-sectional area at the target site, or a procedure to be performed on the target site as the analysis conditions.

4. The image processing apparatus according to claim 3, wherein the processing circuitry is configured to change at least one of a position at which the stent is to be arranged, the length of the stent, and the diameter of the stent as the condition of the stent.

5. The image processing apparatus according to claim 4, wherein the processing circuitry is configured to cause the display to display, when at least one of the length and the diameter of the stent is changed as the analysis conditions, at least one of the shortest length and the smallest diameter of the stent having fractional flow reserve in the blood vessel exceeding a predetermined value.

6. The image processing apparatus according to claim 1, wherein the processing circuitry is configured to calculate at least one of fractional flow reserve, pressure, a flow rate of blood, a flow speed of blood, a vector, and a shear stress at respective positions in the blood vessel as the index value relating to blood flow.

7. The image processing apparatus according to claim 1, further comprising a memory configured to store correspondence information in which a treatment content for the target site and a change in the analysis conditions according to the treatment content are associated with each other, wherein
   the processing circuitry is configured to change the analysis conditions for the fluid analysis based on the correspondence information.

8. An image processing apparatus comprising:
   processing circuitry configured to
   generate blood vessel shape data based on image data including a blood vessel;
   set boundary conditions and analysis conditions in a fluid analysis;
   perform a fluid analysis based on the boundary conditions and the analysis conditions on the blood vessel shape data to calculate an index value relating to blood flow in the blood vessel;
   specify a plurality of target sites in the blood vessel in the image data;
   change pressure conditions used for the fluid analysis on the target sites without changing the blood vessel shape data to calculate an index value relating to blood flow under the changed analysis conditions for the target sites; and
   cause a display to display, in a comparative manner, the index value relating to blood flow before and after the change in the pressure conditions.

9. The image processing apparatus according to claim 8, further comprising a memory configured to store correspondence information in which a treatment content for the target site and a change in the pressure conditions according to the treatment content are associated with each other, wherein the processing circuitry is configured to change the pressure conditions used for the fluid analysis based on the correspondence information.

10. A medical image diagnostic apparatus comprising:
processing circuitry configured to
- acquire image data including a blood vessel;
- generate blood vessel shape data based on the image data including the blood vessel;
- set boundary conditions and analysis conditions in a fluid analysis;
- perform a fluid analysis based on the boundary conditions and the analysis conditions on the blood vessel shape data to calculate an index value relating to blood flow in the blood vessel;
- specify a plurality of target sites in the blood vessel in the image data;
- change pressure conditions used for the fluid analysis on the target sites without changing the blood vessel shape data to calculate an index value relating to blood flow under the changed analysis conditions for the target sites; and
- cause a display to display, in a comparative manner, the index value relating to blood flow before and after the change in the pressure conditions.

11. A medical image diagnostic apparatus comprising:
processing circuitry configured to
- acquire image data including a blood vessel;
- generate blood vessel shape data based on the image data including the blood vessel;
- set boundary conditions and analysis conditions in a fluid analysis;
- perform a fluid analysis based on the boundary conditions and the analysis conditions on the blood vessel shape data to calculate an index value relating to blood flow in the blood vessel;
- specify a plurality of target sites in the blood vessel in the image data;
- change analysis conditions for the fluid analysis corresponding to positions of the target sites without changing the blood vessel shape data to calculate an index value relating to blood flow under the changed analysis conditions for the target sites; and
- cause a display to display, in a comparative manner, the index value relating to blood flow calculated under the changed analysis conditions for the target sites.

\* \* \* \* \*